United States Patent [19]
Yao et al.

[11] Patent Number: 5,886,131
[45] Date of Patent: Mar. 23, 1999

[54] METHOD FOR PREPARING 1,4-BIS(4-AMINOPHENOXY)NAPHTHALENE AND ITS POLYMERS

[75] Inventors: Shin Chuan Yao; Jongfu Wu; Kun-Lin Cheng; Wen-Tung Chen, all of Taipei Hsien, Taiwan

[73] Assignee: China Textile Institute, Taipei Hsien, Taiwan

[21] Appl. No.: 866,121

[22] Filed: May 30, 1997

[51] Int. Cl.⁶ .......................... C08G 73/10; C07C 217/90
[52] U.S. Cl. .......................... 528/185; 528/125; 528/128; 528/170; 528/171; 528/172; 528/173; 528/174; 528/176; 528/179; 528/183; 528/188; 528/220; 528/229; 528/310; 528/322; 528/332; 528/335; 528/336; 528/350; 528/353; 564/428

[58] Field of Search ....................................... 528/310, 185, 528/171, 176, 173, 172, 188, 220, 229, 350, 353, 174, 322, 332, 125, 128, 170; 564/428

[56] References Cited

U.S. PATENT DOCUMENTS 5,340,904  8/1994  Yang et al. .............................. 528/185
5,478,913  12/1995  Boyce et al. ............................ 528/185

*Primary Examiner*—P. Hampton-Hightower
*Attorney, Agent, or Firm*—Rosenberg, Klein & Bilker

[57] ABSTRACT

A method for synthesizing 1,4-bis(4-aminophenoxy)naphthalene and a series of polyamides, polyimides and copoly(amide-imide)s derived from the said compound is disclosed. These polymers possess excellent thermal stability and mechanical strength.

5 Claims, No Drawings

METHOD FOR PREPARING 1,4-BIS(4-AMINOPHENOXY)NAPHTHALENE AND ITS POLYMERS

FIELD OF THE INVENTION

This invention concerns about 1,4-bis(4-aminophenoxy) naphthalene and related series of polyamides, plyimides and copoly(amide-imide)s prepared therefrom.

DESCRIPTION OF RELATED ART

In the field of high performance polymers, aromatic diamines have been widely used in the manufacture of polymers of superior properties, for instance, Kevlar from p-phenylenediamine and Nomex from m-phenylenediamine. The well-known Kapton® from Du Pont Co. is manufactured from 4,4'-diaminophenyl ether and pyromellitic dianhydride.

As a by-product of coal tar, naphthalene has been extensively used in the preparation of dyestuff intermediates and insecticides. Due to the large quantity of production, research and development are required to exploit new applications of naphthalene. For certain industries, high performance polymers with unique thermal stability and rigidity are required in various applications. Examples of such polymers include polyether-sulfone, polyetherketone, liquid crystals polyester, amorphous polyesters, polyamides and polyimides. Most of these polymers contain naphthalene ring in the molecular structure thereof, which provides a better heat resistance and rigidity. As to the past research, diamines based on bis(phenoxy)naphthalene are prepared by using dihydroxynaphthalenes and p-chloronitrobenzene to form dinitro compounds under alkaline environment and then followed by reduction to diamines. References related to the prior art technique include:

(A) U.S. Pat. No. 5,340,904 and Taiwan patent publication No. 223085 which disclose the synthesis of bis (aminophenoxy)naphthalene with substitution groups in (1,5),(1,6),(1,7),(2,3),(2,6) and (2,7) in the naphthalene ring.

(B) U.S. Pat. No. 5,076,817, which teaches the use of 2,7-bis(aminophenoxy)naphthalene.

(C) Chemical Abstract Vol.117:191511j, which describes using 1,6-dihydroxynaphthalene and p-chloronitrobenzene as raw materials to synthesize 1,6(4-aminophenoxy)naphthalene.

(D) Japanese patent No. 33166(1989) which discloses a method of using 2,6-(4-aminophenoxy)naphthalene to prepare soluble polyimides which method was used by Toa Nenryo Kogyo, Japan, in 1989.

It is known so far and from the techniques mentioned above, 1,4-bis(4-aminophenoxy)naphthalene and the derived polymers thereof have never been shown in any papers or references.

DESCRIPTION OF THE INVENTION

In the synthesis of 1,4-bis(4-aminophenoxy)naphthalene, it is not possible to use the traditional nucleophilic reaction of p-chloronitrobenzene with 1,4-dihydroxynaphthalene. The nucleophilic reaction has to be carried out between p-fluoronitrobenzene and 1,4-dihydroxynaphthalene to form dinitro compound followed by reduction to diamine. Thus, the method is an innovation for the said compound.

It accordance with the invention, 1,4-bis(4-aminophenoxy)naphthalene is synthesized first and then the diamine is used to prepare aramide, polyimidies and copoly (amide-imide)s. This series of polymers possess good heat resistance and mechanical properties.

The structures of 1,4-bis(4-aminophenoxy)naphthalene and polymers thereof are as follows:

(1) Diamine:
1,4-bis(4-aminophenoxy)naphthalene 1,4-bis(4-aminophenoxy)naphthalene

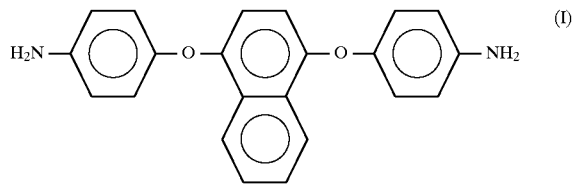

(2) Polyamide:

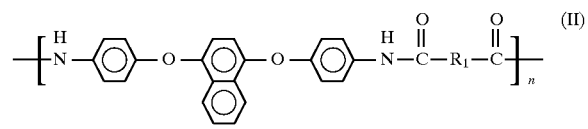

in (II), $R_1$ represents

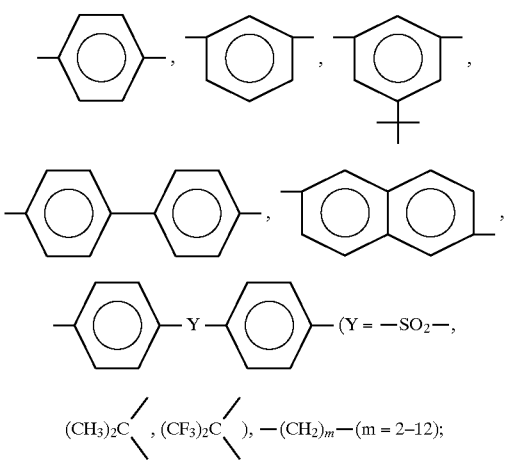

and n is an integer between 10–600.

(3) Polyimide

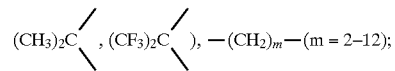

in (III), $R_2$ represents

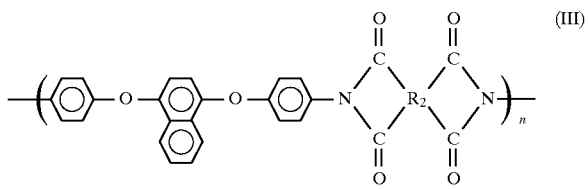

-continued
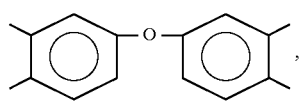
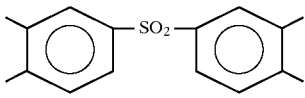
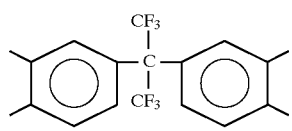
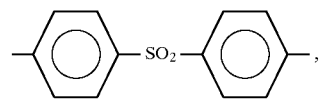
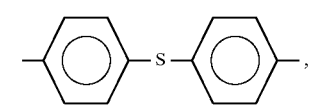
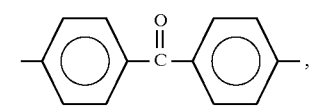
(4) Polyamide-imide
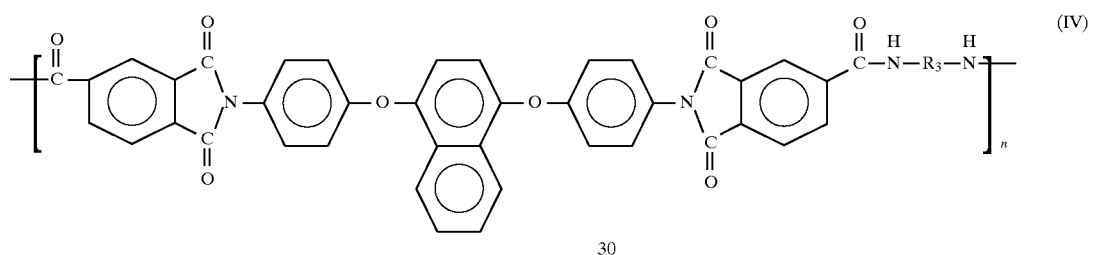
(IV)
in (IV), R₃ represents
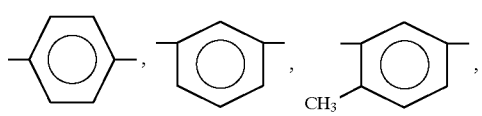
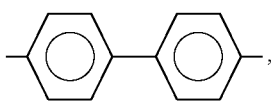
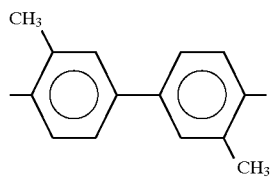
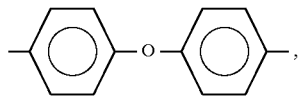
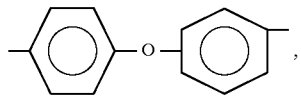
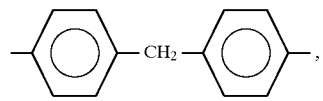
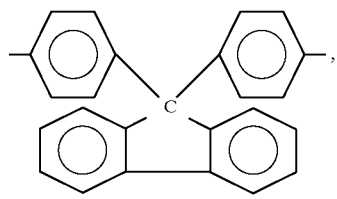
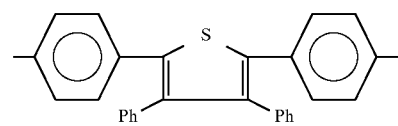
(5) Copoly(amide-imide)

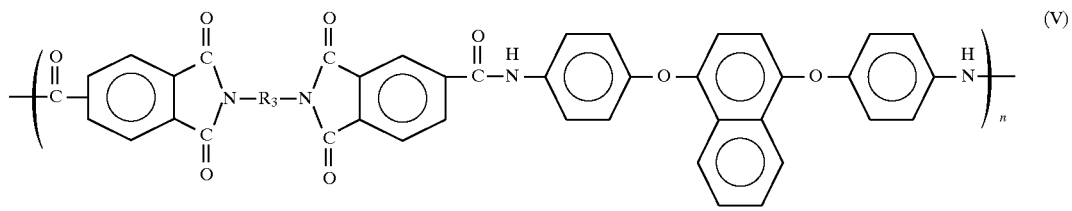

(V)

in (V), $R_3$ is the same as that in (IV).

Preparation of Diamine and its Polymers (1) Diamine: 1,4-bis(4-aminophenoxy)naphthalene (I)

The feature of this diamine is a symmetrical structure with two phenoxy groups respectively in (1,4) positions in the naphthalene ring. This diamine is a new compound with no previous report in literature.

Through the condensation of 1,4-dihydroxynaphthalene and p-fluoronitrobenzene followed by hydrogenation, (I) can be synthesized accordingly:

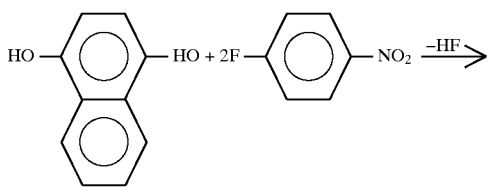

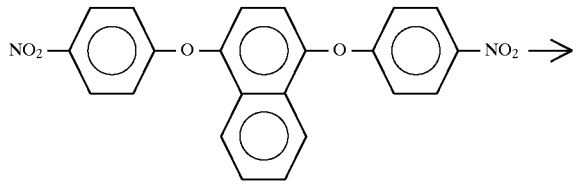

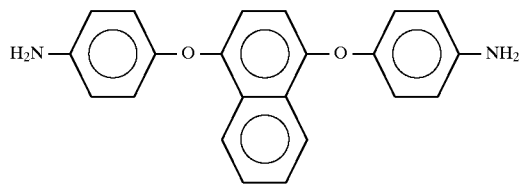

The dehydrofluorination condensation can be performed by heating in polar solvent under alkaline condition. Reduction of the nitro groups can be done either by hydrogenation in the presence of metallic reducing catalyst(Pd catalyst) or by using hydrazine as reducing agent to obtain (I).

(2) Polyamide (II)

Polyamide (II) has bis(phenoxy)naphthalene units in the polymer backbone. Its synthesis is carried out with polycondensation of diamine(I) with dicarboxylic acid or its activated form. For direct reaction with dicarboxylic acid, the polycondensation can be performed in the presence of condensing agent, the most suitable one being triphenyl phosphite-pyridine system. With the activated form of dicarboxylic acid, such as diacyl chloride, amide-type polar solvent such as dimethylacetamide(DMAc) or N-methylpyrrolidone(NMP) can be used directly in the reaction as following:

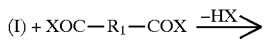

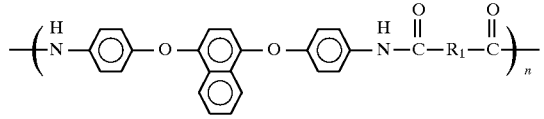

where X represents OH or Cl and $R_1$ as shown in (II).

(3) Polyimide(III)

Polyimide(III) is a series of polymers containing sequence of bis(phenoxy)naphthalene units. Its preparation is done by the polyaddition of the diamine(I) with aromatic dianhydride in a suitable organic solvent to form polyamic acid, which is further heated or dehydrated (using acetic anhydride) to proceed intramolecular polycondensation to form polyimide as shown in following reactions:

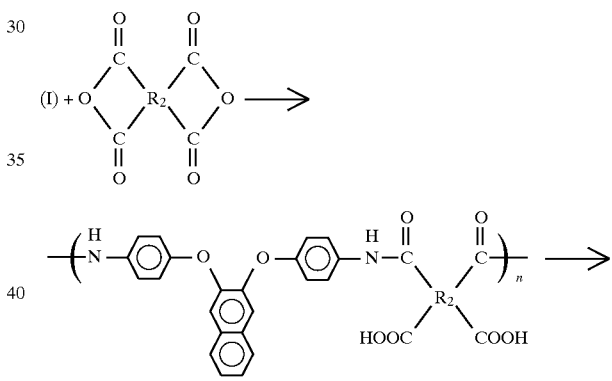

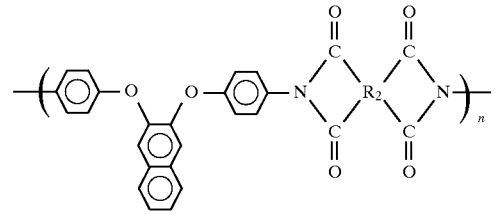

where $R_2$ represents those shown in (III).

(4) Poly(amide-imide) (IV)

The poly(amide-imide)(IV) is related to the trimellitic anhydride(TMA) and can be condensated from the 1 mole diamine(I) and 2 mole TMA to obtain the diimide-diacid which is then polycondensated with the aromatic diamine into the poly(amide-imide)(IV) of the alternating type. The polymer(IV) were synthesized from the direct polycondensation of the imide ring-preformed dicarboxylic acid(VI) and various diamines by using triphenyl phosphite and pyridine as condensing agent.

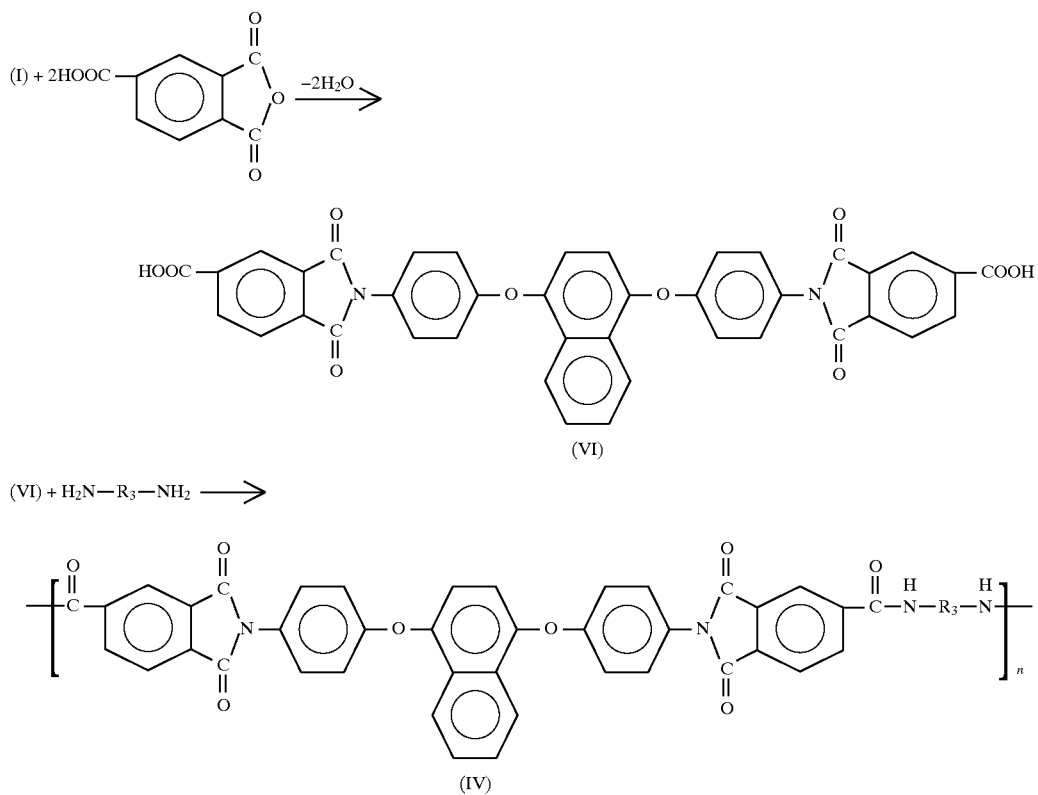

Where R₃ is the same as those for (IV).

(5) Copoly(amide-imide) (V)

Copoly(amide-imide) (V) is a series of polymers based on trimellitic anhydride(TMA).

The condensation of a series of diamines with TMA forms a series of dicarboxylic acids(VII). These diimide-diacids were polymerized with diamine(I) to prepare polymer(V) by using triphenyl phosphite/pyridine as condensing agent, as shown in the following:

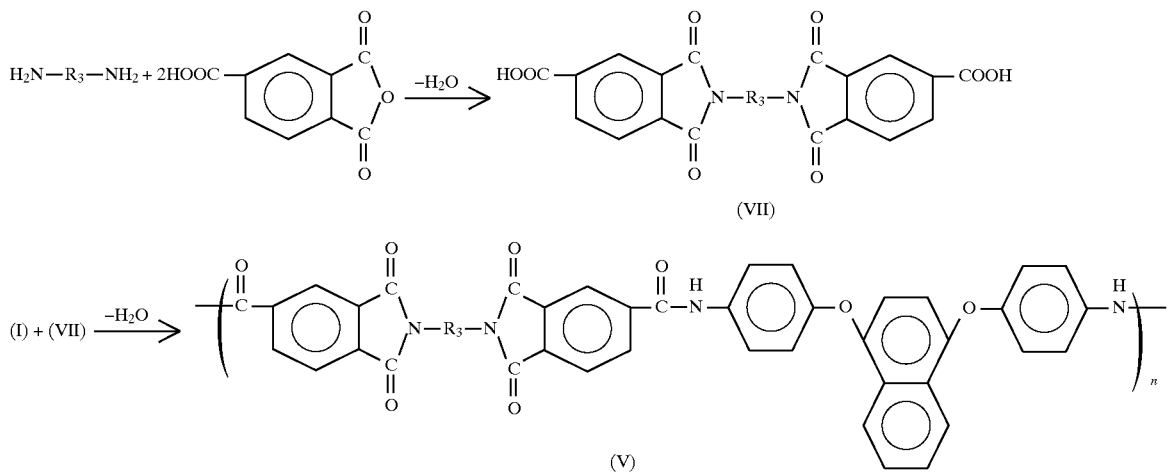

where R₃ represents those for (IV).

PRACTICE EXAMPLES:

Case 1

Preparation of 1,4-bis(4-aminophenoxy)naphthalene

In 500 ml flask, 30 g of 1,4-dihydroxynaphthalene, 56 g of p-fluoronitrobenzene, 60 g anhydrous potassium carbonate, and 160 ml of N,N-dimethylformamide(DMF) were refluxed with stirring for eight hours at 110° C. After cooling, pour the reaction mixture into a mixture of 500 ml methanol-water(volume ratio 1:1). Filter off the separated brown powder and wash thoroughly with methanol and warm water. The powder after drying weighed 70 g(m.p.187°–190° C., yield 93%)as the dinitro precursor, which can be re-crystallized from glacial acetic acid to obtain brown crystals (m.p. 191° C.).

Elemental analysis: Calculated values: C: 69.56% H: 3.21% N: 4.06% Found values: C: 69.41% H 3.30% N: 4.02%

Molecular structure

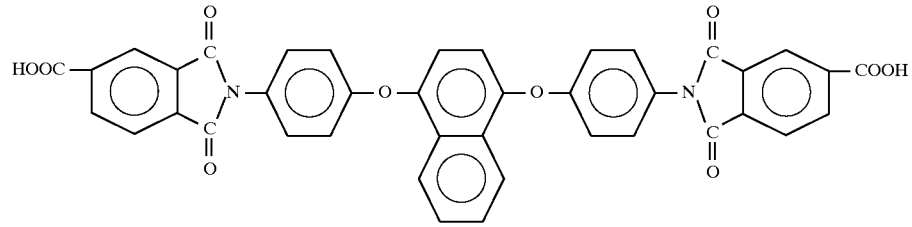

61 g of 1,4-bis(4-nitrophnoxy)naphthalene,0.3 g of Pd catalyst and 400 ml of ethanol were introduced into the three-neck flask to which 150 ml of hyydrazine monohydrate was added dropwise over a period of 3 hours at 80° C. Filter the mixture while warm and pour the filtrate into ice water. The separated brownish yellow powder so obtained is weighed 43 g (yield 84%, m.p. 158° C).

Elemental analysis: Calculated values: C:77.19% H: 5.26% N: 8.18% Found values C:77.09% H: 5.37% N: 8.10%
Molecular structure

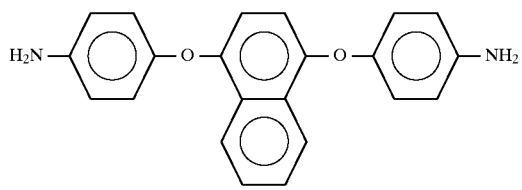

Case 2

Preparation of 1,4-bis(4-trimellitimidophenoxy) naphthalene

A mixture of 6.8 g of 1,4-bis(4-aminophenoxy) naphthalene and 8.2 g of trimellitic anhydride were dissolved in 30 ml of dry DMF at 60° C. and stirred for 1 hour. About 30 ml of toluene was then added, and the mixture was heated with reflux for 3 hours until about 0.72 ml of water was distilled off azeotropically under a Dean-Stark trap. After completing the reaction, remove toluene by distillation. During cooling yellow solid begins to separate out, which is filtered and washed thoroughly with methanol to obtain 13 g of solid product(yield 94%, m.p.>400° C.).

Case 3

Polyamide (II)

In a single-neck 50 ml flask, a mixture of 0.427 g (1.25 mmol) of 1,4-bis(4-aminophenoxy)naphthalene, 0.27 g of (1.25 mmol) of 2,6-naphthalenedicarboxylic acid 0.25 g of calcium chloride, 4 ml of N-methyl-2-pyrrolidone, 0.7 ml of pyridine and 0.8 ml of triphenyl phosphite was heated at 100° C. in an oil bath for three hours to form a viscous polymer. The obtained polymer solution was trickled on 500 ml of methanol giving rise to a stringy precipitate, which is washed thoroughly with methanol and warm water. The yield is 0.65 g (99.9%).

The inherent viscosity of a 0.5 g/dl polymer solution in DMAc was 1.1 dl/g at 30° C. The results of elemental analysis, mechanical strength, heat resistance and molecular structure are as follows:

Elemental analysis: $(C_{34}H_{22}N_2O_4)n$ Calculated values: C: 78.19% H: 4.24% N: 5.36% Found values: C 78.3% H: 4.12% N: 5.43%
Mechanical strength
  Yield strength 75 Mpa
  Elongation at break 7%
  Initial modulus 1.7 Gpa
  Temperature for 10% weight loss
  in nitrogen 528° C.
  in oxygen 489° C.
Molecular structure

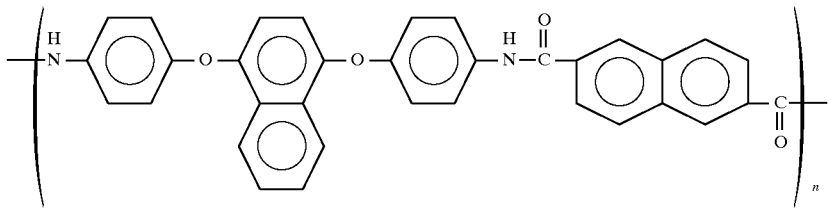

Case 4
Polyimide(III)

To a solution of 0.856 g(2.5 mmol) of 1,4-bis(4-aminophenoxy)napathalene in 13.5 ml of DMAc, was added gradually 0.734(2.5 mmole) of 3,3',4,4'-biphenyltetracarboxylic dianhydride. The mixture was stirred with ice water bath. The inherent viscosity of this polyamic acid is ζ inh=0.95 dl/g (0.5 g/dl in DMAc at 30° C.).

The poly(amic acid) solution thus obtained was spread to a certain thickness and evaporated at 80° C. to remove solvent and form a membrane. Imidization was carried out by thermal cyclodehydration of the poly(amic acid) film by sequential heating at 110° C., 150° C., 200° C., 230° C. and 250° C. for 15 minutes each, respectively. The results of elemental analysis, mechanical strength, heat resistance and molecular structure are as follows:

Elemental analysis: $(C_{38}H_{20}N_2O_7)n$ Calculated values: C: 74.02% H: 3.27% N: 4.54% Found values: C: 74.10% H: 3.29% N: 4.67%

Mechanical strength
    Tensile strength 115 Mpa
    Elongation at break 12%
    Initial modulus 1.95 Gpa
    Temperature for 10% weight loss:
    in nitrogen 575° C.
    in oxygen 569° C.
Molecular structure

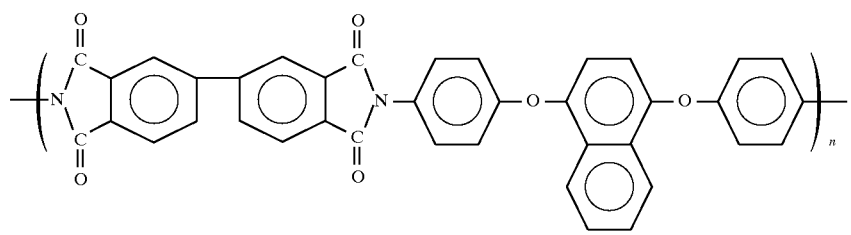

Case 5
Polyamide-imide(IV)

In a 50 ml single-neck flask, a mixture of 0.86 g (1.25 mmol) of 1,4-bis (4-trimellitimido-phenoxy)naphthalene (VI), 0.1355 g (1.25 mmol) of m-phenylenediamine, 8 ml of N-methyl-2-pyrrolidone(NMP), 0.8 g of calcium chloride, 1.6 g pyridine and 0.8 ml of triphenyl phosphite were heated with stirring at 100° C. for 3 hours to obtain a viscous liquid, which is poured into stirred methanol. The resulting fibrous polymer is thoroughly washed with methanol and warm water with a yield of 0.953 g after drying (100%). Its inherent viscosity is ζ inh=1.50 dl/g (0.5 g/dl in DMAc at 30° C.). The results of elemental analysis, mechanical strength, heat resistance and molecular structure are as follows:

Elemental analysis: $(C_{46}H_{26}N_4O_8)n$ Calculated values C: 72.43% H: 3.43% N: 7.34% Found values C: 72.51% H: 3.61% N: 7.50%

Mechanical strength
    Yield strength 76 Mpa
    Elongation at break 8%
    Initial modulus 1.6 Gpa
    Temperature for 10% weight loss:
    in nitrogen 566° C.
    in air 530° C.
Molecular structure Case 6
Copoly(amide-imide) (V)

In a 300 ml flask, 0.02 mmol of m-phenylenediamine, 0.04 mmol of trimellitic anhydride and 40 ml of N,N'-dimethylformamide(DMF) were stirred at 40° C. for dissolution. Then add 20 ml of toluene for azeotropic reflux to remove water in four hours. After cooling and adding methanol, diimide-diacid separates out quantitatively as 1,3-bis(4-trimellitimidocarboxy)benzene(VII).

In a 50 ml single-neck flask, a mixture of 0.57 g (1.25 mmol) of (VII) and 0.427 g of 1,4-bis(4-aminophenoxy) naphthalene in the presence of 0.8 g calcium chloride, 8 ml of N-methyl-2-pyrrolidone, 1.6 ml of pyridine and 0.8 ml of triphenyl phosphite was heated with stirring at 100° C. The viscous liquid so obtained is poured into stirred methanol to obtain fibrous polymer, with a yield of 0.948 g(99%) after thoroughly washed with methanol and hot water and drying. Its inherent viscosity is ζ inh=0.90 dl/g.

Its membrane prepared from DMAc solution has the following characteristics:

Mechanical strength

Tensile strength 76 Mpa

Elongation at break 8%

Initial modulus 2.0 Gpa

Temperature for 10% weight loss:

in nitrogen 570° C.

in air 550° C.

Molecular structure

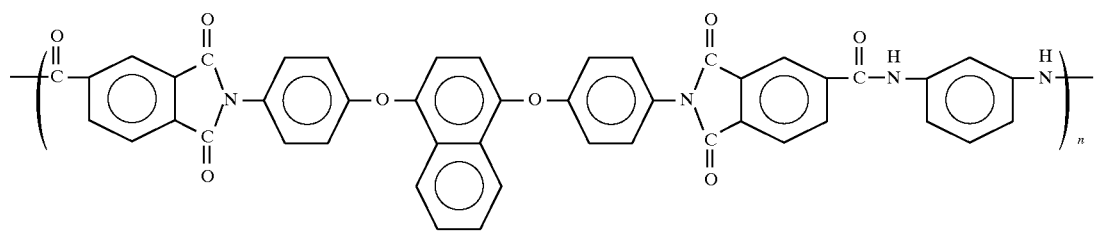

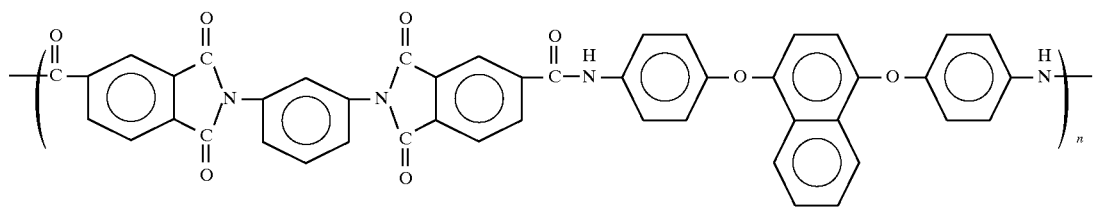

This invention, as described above, is capable to synthesize 1,4-bis(4-aminophenoxy)naphthalene and to prepare a series of polyamides, polyimides and copoly(amide-imide)s from this compound. Such polymers having excellent heat resistance and mechanical strength can serve various applications.

We claim:

1. A 1,4-Bis(4-aminophenoxy)naphthalene comprising the following chemical structure shown in (I) as below:

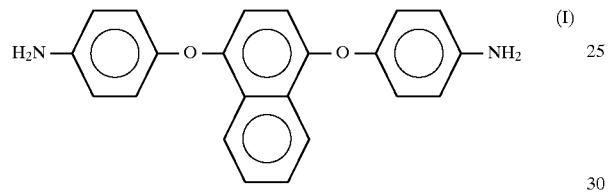

2. A polyamide comprising the following chemical structure shown in (II) below

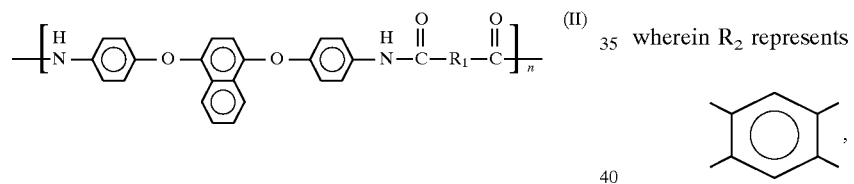

wherein said $R_1$ represents

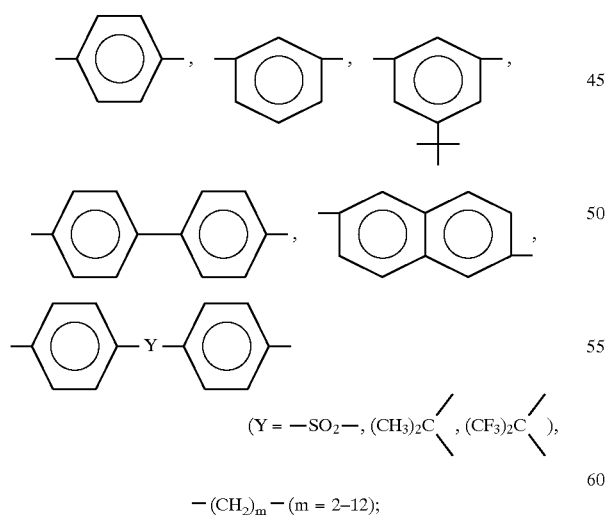

$(Y = -SO_2-, (CH_3)_2C{<}, (CF_3)_2C{<})$, $-(CH_2)_m-$ (m = 2–12);

and n is an integer between 10–600.

3. A polyimide comprising the following chemical structure shown in (III) as below:

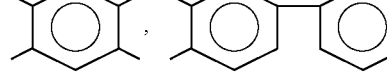

wherein $R_2$ represents

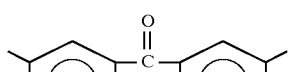

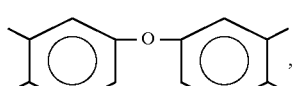

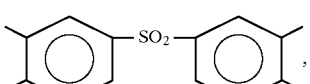

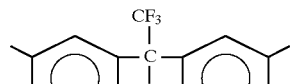

4. A polyamide-imide comprising the following chemical structure shown in (IV) below:

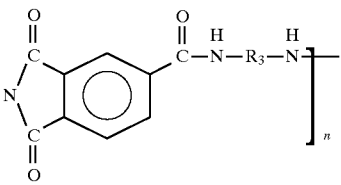
wherein $R_3$ represents
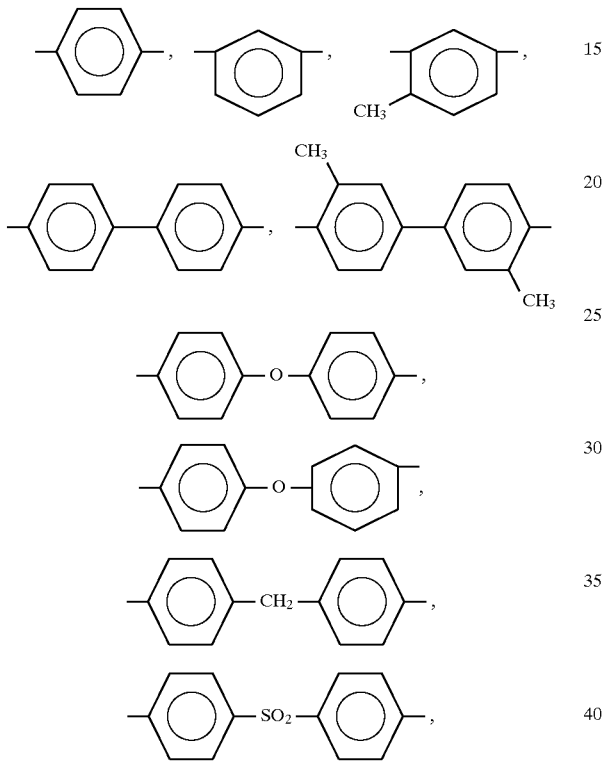
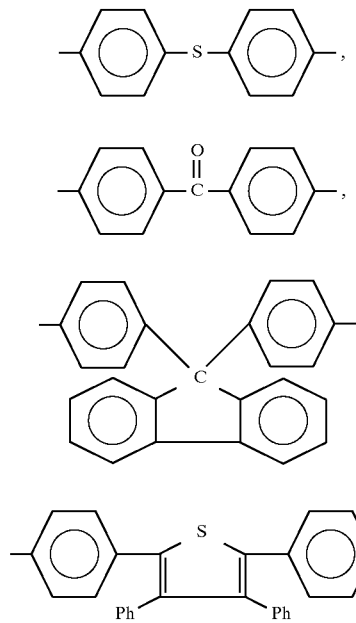
5. A copoly(amide-imide) comprising the following chemical structure shown in (V) as below:
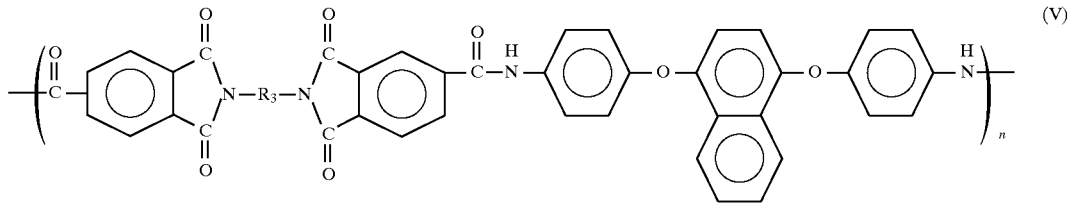
where $R_3$ is the same as in (IV).
* * * * *